(12) United States Patent
Lan et al.

(10) Patent No.: US 11,071,803 B1
(45) Date of Patent: Jul. 27, 2021

(54) ULTRAVIOLET STERILIZATION LINE LAMP

(71) Applicant: SHENZHEN GUANKE TECHNOLOGIES CO., LTD, Shenzhen (CN)

(72) Inventors: Qing Lan, Shenzhen (CN); Tianlong Dai, Shenzhen (CN); Shoubao Chen, Shenzhen (CN); Ligen Liu, Shenzhen (CN)

(73) Assignee: SHENZHEN GUANKE TECHNOLOGIES CO., LTD, Shenzhen (CN)

(*) Notice: Subject to any disclaimer, the term of this patent is extended or adjusted under 35 U.S.C. 154(b) by 0 days.

(21) Appl. No.: 17/069,141

(22) Filed: Oct. 13, 2020

(30) Foreign Application Priority Data

Aug. 31, 2020 (CN) .......................... 202010907326.8

(51) Int. Cl.
*A61L 9/20* (2006.01)
*F21V 15/02* (2006.01)
*F21S 8/06* (2006.01)

(52) U.S. Cl.
CPC . *A61L 9/20* (2013.01); *F21S 8/06* (2013.01); *F21V 15/02* (2013.01); *A61L 2202/11* (2013.01)

(58) Field of Classification Search
None
See application file for complete search history.

(56) References Cited

U.S. PATENT DOCUMENTS

| | | | | |
|---|---|---|---|---|
| 7,674,436 | B1* | 3/2010 | Feldman | A61L 9/205 422/121 |
| 10,143,956 | B2* | 12/2018 | Hayden | B01D 53/18 |
| 10,329,180 | B2* | 6/2019 | Hayden | A61L 9/00 |
| 11,013,822 | B1* | 5/2021 | Woodward | A61L 2/202 |
| 2006/0177356 | A1* | 8/2006 | Miller | A61M 11/06 422/121 |
| 2009/0311951 | A1* | 12/2009 | Walkinshaw | F24F 5/0085 451/261 |
| 2011/0033346 | A1* | 2/2011 | Bohlen | A61L 9/205 422/186.3 |
| 2012/0171079 | A1* | 7/2012 | Morito | B01J 35/004 422/121 |
| 2013/0291735 | A1* | 11/2013 | Livchak | F24F 1/01 96/224 |

(Continued)

*Primary Examiner* — Andrew Smyth
(74) *Attorney, Agent, or Firm* — Maier & Maier, PLLC

(57) ABSTRACT

An ultraviolet sterilization line lamp is disclosed. The ultraviolet sterilization line lamp includes a lamp body, the lamp body being elongated, two sides of the lamp body being provided with two accommodating grooves; two grilles connected to the lamp body and respectively located in the two accommodating grooves, inner wall surfaces of each of the grilles and each of the accommodating grooves forming a sterilization cavity, each of the grilles including light exit grooves communicating with the sterilization cavity, each of the light exit grooves extending from one end of a corresponding grille close to the lamp body to another end of the corresponding grille away from the lamp body, an inner wall surface of each of the light exit grooves being provided with a light-absorbing layer; and two ultraviolet sterilization modules connected to the lamp body or the grille, and respectively located in two sterilization cavities.

15 Claims, 9 Drawing Sheets

(56) References Cited

U.S. PATENT DOCUMENTS

| | | | | |
|---|---|---|---|---|
| 2017/0321877 | A1* | 11/2017 | Polidoro | F21V 33/0088 |
| 2018/0250430 | A1* | 9/2018 | Machovina | B01D 53/0407 |
| 2018/0347574 | A1* | 12/2018 | Niemiec | F21S 10/06 |
| 2019/0072288 | A1* | 3/2019 | Niemiec | F21V 33/0096 |
| 2019/0292315 | A1* | 9/2019 | Niemiec | C09K 19/3814 |
| 2019/0360680 | A1* | 11/2019 | Niemiec | F21V 29/677 |
| 2020/0289698 | A1* | 9/2020 | Polidoro | F21V 21/04 |
| 2020/0289984 | A1* | 9/2020 | Drake | A61L 9/20 |
| 2020/0289985 | A1* | 9/2020 | Drake | A61L 9/20 |
| 2020/0354513 | A1* | 11/2020 | Niemiec | F04D 25/088 |
| 2021/0052764 | A1* | 2/2021 | Terkelsen | A61L 9/20 |
| 2021/0093746 | A1* | 4/2021 | Yamaguchi | A61L 9/205 |
| 2021/0106711 | A1* | 4/2021 | Wang | F24F 8/194 |

\* cited by examiner

ULTRAVIOLET STERILIZATION LINE LAMP

CROSS-REFERENCE TO RELATED APPLICATIONS

The present patent application claims benefit and priority to Chinese Application No. 2020109073268 filed on Aug. 31, 2020 which is hereby incorporated by reference into the present disclosure.

TECHNICAL FIELD

The present disclosure relates to the technical field of sterilization lamp equipment, in particular to an ultraviolet sterilization line lamp.

BACKGROUND

Commonly, the ultraviolet lamp tube of the ultraviolet lamp is open, which causes the ultraviolet light to directly irradiate the entire environment to be sterilized when the ultraviolet lamp is working. Since ultraviolet rays are very harmful to the human body, when there are people in the environment, in order to avoid damage to the human body, it is necessary to stop using the ultraviolet lamp, which makes it impossible to use the ultraviolet lamp for environmental sterilization.

Ultraviolet lamp has a good sterilization effect, but it usually requires people to leave the sterilization place, otherwise it will cause harm to people. To ensure human safety, a human body induction control device can be designed on the UV lamp to ensure that the UV lamp stops working when someone is present; the ultraviolet lamp can also be provided in the sealing cavity, and air is sucked into the sealing cavity through the fan module, and then discharged after being sterilized by the ultraviolet lamp to complete the sterilization. The safety of the former scheme depends on the accuracy and stability of the induction control device, and when there are people in the sterilization place for a long time, it is difficult for the ultraviolet lamp to turn on the sterilization mode, which affects the use. The latter solution requires air to be sucked into the sealing cavity through the fan module to kill the virus, the sterilization effect is related to the power of the fan module and the air circulation capacity, and the energy consumption is high, and it is prone to generate louder noise. Besides, since ultraviolet rays cannot be directly irradiated to open sterilization places, the sterilization effect is much worse than when ultraviolet rays are directly exposed and used in sterilization places.

The above content is only used to assist the understanding of the technical solution of the present disclosure, and does not mean that the above content is recognized as prior art.

SUMMARY

The main objective of the present disclosure is to provide an ultraviolet sterilization line lamp, which aims to improve the safety of the ultraviolet sterilization line lamp and improve the sterilization effect.

In order to achieve the above objective, the present disclosure provides an ultraviolet sterilization line lamp, including:

a lamp body, the lamp body being elongated, two sides of the lamp body being provided with two accommodating grooves;

two grilles connected to the lamp body and respectively located in the two accommodating grooves, inner wall surfaces of each of the grilles and each of the accommodating grooves forming a sterilization cavity, each of the grilles including light exit grooves communicating with the sterilization cavity, each of the light exit grooves extending from one end of a corresponding grille close to the lamp body to another end of the corresponding grille away from the lamp body, an inner wall surface of each of the light exit grooves being provided with a light-absorbing layer; and two ultraviolet sterilization modules connected to the lamp body or the grille, and respectively located in two sterilization cavities.

In an embodiment of the present disclosure, taking a central symmetry plane of the lamp body as a reference plane, the two accommodating grooves are mirror images of the reference plane;

each of the grilles includes light-absorbing plates along a length of the lamp body, an extension surface of each of the light-absorbing plates is perpendicular to the reference plane, two adjacent light-absorbing plates are spaced apart and configured to form a light exit groove;

a surface of each of the light-absorbing plates is provided with the light-absorbing layer; and each of the two accommodating grooves is configured as a reflective surface.

In an embodiment of the present disclosure, each of the light-absorbing plates is provided with a bending portion at one end adjacent to a corresponding ultraviolet sterilization module.

In an embodiment of the present disclosure, the lamp body is further provided with a through hole communication with the two accommodating grooves; and the ultraviolet sterilization line lamp further includes a fan module provided on the lamp body and located at the through hole.

In an embodiment of the present disclosure, a limiting space is provided on a periphery of the through hole;

the fan module includes a mounting bracket and a fan connected to the mounting bracket, the mounting bracket is provided with an escape space corresponding to the fan, an outer wall surface of the mounting bracket is provided with a clamping portion, and the clamping portion is configured to abut against an inner wall surface of the limiting space.

In an embodiment of the present disclosure, the lamp body is provided with two first shaft holes corresponding to the two accommodating grooves; and each of the grilles is provided with a second shaft hole, a rotating shaft passes through one of the two first shaft holes and the second shaft hole corresponding to one of the first shaft holes to rotationally connect the two grilles with the lamp body.

In an embodiment of the present disclosure, the lamp body is provided with a first insertion hole communicating with the accommodating groove, and the grille is provided with a second insertion hole corresponding to the first insertion hole; and the ultraviolet sterilization line lamp further includes a fixing pin penetrating through the first insertion hole and the second insertion hole to lock the grille and the lamp body.

In an embodiment of the present disclosure, the lamp body is provided with a sliding hole communicating with the accommodating groove, and the sliding hole is spaced apart from the first insertion hole; the ultraviolet sterilization line lamp further includes a limiting block slidably disposed on the sliding hole; the ultraviolet sterilization line lamp has an unfolded state, in the unfolded state, the grille is configured to rotate relative to a first frame and be away from the accommodating groove, and the limiting block is configured to extend relative to the sliding hole and abut against the grille; and/or the lamp body is further provided with an elastic column provided on a surface of the accommodating groove facing the grille.

In an embodiment of the present disclosure, the ultraviolet sterilization module includes an ultraviolet sterilization lamp, a connection terminal, two buffer rings and two pressing rings; the two buffer rings are sleeved on an outer surface of a lamp cap of the ultraviolet sterilization lamp, the two pressing rings are connected to an inner wall surface of the sterilization cavity, thereby the pressing ring is cooperated with the buffer ring to position the ultraviolet sterilization lamp in the sterilization cavity, and the connection terminal is electrically connected to the ultraviolet sterilization lamp; and/or a surface of the accommodating groove facing the ultraviolet sterilization module is a concave arc surface.

In an embodiment of the present disclosure, the ultraviolet sterilization line lamp further includes a sensor, sensing ports of the sensor are provided on two sides of the lamp body, and the sensor and the grille are spaced apart; and/or the lamp body has an up-down direction, the ultraviolet sterilization line lamp further includes a sensor, a sensing port of the sensor is provided on a surface below the lamp body, and the sensor is located below the grille; and/or the lamp body has an up-down direction, and the ultraviolet sterilization line lamp further includes a light-emitting module provided on a surface below the lamp body and located below the grille; and/or the ultraviolet sterilization line lamp further includes a control panel provided at an end of the lamp body.

In technical solutions of the present disclosure, the two grilles are provided on opposite sides of the lamp body, and the ultraviolet sterilization module is provided between the lamp body and the grille, such that the ultraviolet rays generated by the ultraviolet sterilization module are emitted toward the grille on both sides of the lamp body to form a semi-exposed irradiation structure. Ultraviolet sterilization line lamps are usually hoisted or directly installed on the top ceiling to prevent ultraviolet rays from irradiating the human body and improve the safety of the ultraviolet sterilization line lamp. In addition, one end of the light exit groove of the grille is away from the lamp body, so that ultraviolet rays can be directly emitted into the environment outside the lamp, and the sterilization effect of the air in the surrounding environment of the grille is improved. Ultraviolet rays are directly emitted towards the areas corresponding to the two grilles to increase the sterilization range of ultraviolet rays on the air in the environment. Meanwhile, under the action of air convection, the sterilized air can be discharged as soon as possible and the unsterilized air can enter the sterilization area directly exposed to ultraviolet rays as soon as possible, thereby improving the sterilization efficiency of the overall space. Even without a fan, a good sterilization effect can be obtained. On the other hand, the light exit grooves are provided on the grille, and the light exit grooves extend from one end of the grille close to the lamp body to the other end of the grille away from the lamp body 1. In other words, the light exit groove of the grille has a longer covering length, and the surface of the light exit groove is provided with a light-absorbing layer that absorbs ultraviolet rays. When the ultraviolet rays are irradiated in the direction of the grille, except for the ultraviolet rays parallel to the inner wall surface of the light exit groove can be emitted from the lamp, other ultraviolet rays will be absorbed by the inner wall surface of the light exit groove, reducing the probability of ultraviolet rays directly irradiating the human body, and enhancing the safety of the ultraviolet sterilization line lamp. The ultraviolet sterilization line lamp of the present disclosure improves the safety of environmental sterilization by ultraviolet rays and improves the sterilization effect.

BRIEF DESCRIPTION OF THE DRAWINGS

In order to more clearly illustrate the embodiments of the present disclosure, drawings used in the embodiments will be briefly described below. Obviously, the drawings in the following description are only some embodiments of the present disclosure. It will be apparent to those skilled in the art that other figures can be obtained according to the structures shown in the drawings without creative work.

DETAILED DESCRIPTION OF THE EMBODIMENTS

The technical solutions of the embodiments of the present disclosure will be described in more detail below with reference to the accompanying drawings. It is obvious that the embodiments to be described are only some rather than all of the embodiments of the present disclosure. All other embodiments obtained by persons skilled in the art based on the embodiments of the present disclosure without creative efforts shall fall within the scope of the present disclosure.

It should be noted that if there are directional indications (such as up, down, left, right, front, rear . . . ) in the embodiment of the present disclosure, the directional indication is only used to explain the relative positional relationship and movement of the components in a specific posture (as shown in the figure). If the specific posture changes, the directional indication will change accordingly.

Besides, the descriptions associated with, e.g., "first" and "second," in the present disclosure are merely for descriptive purposes, and cannot be understood as indicating or suggesting relative importance or impliedly indicating the number of the indicated technical feature. Therefore, the feature associated with "first" or "second" can expressly or impliedly include at least one such feature. In addition, the meaning of "and/or" appearing in the disclosure includes three parallel scenarios. For example, "A and/or B" includes only A, or only B, or both A and B. The technical solutions between the various embodiments can be combined with each other, but it must be based on what can be achieved by a person of ordinary skill in the art. When the combination of technical solutions is contradictory or cannot be achieved, it should be considered that such a combination of technical solutions does not exist, nor does it fall within the protection scope of the present disclosure.

Figure 1:
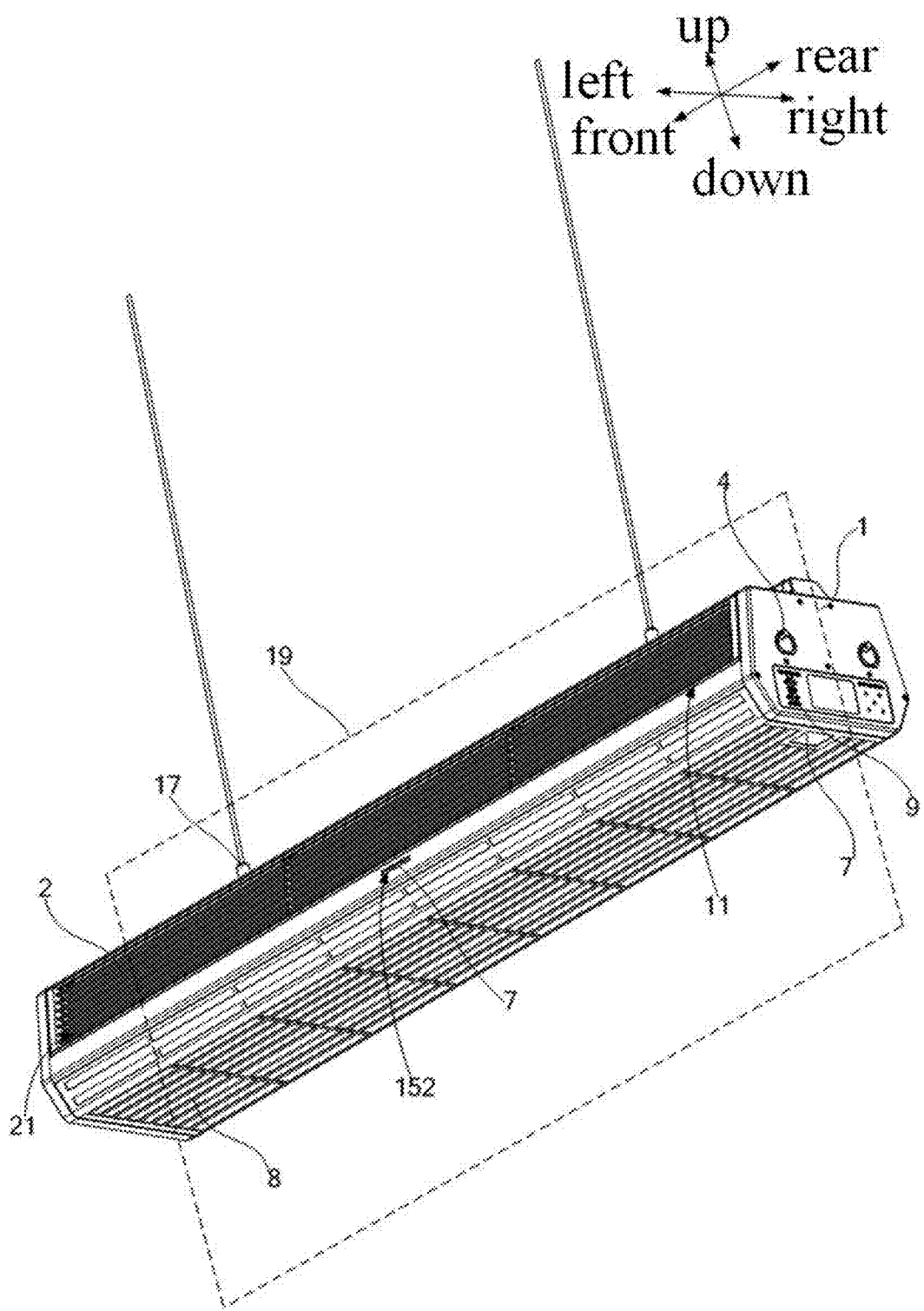
FIG. 1 is a schematic structural diagram of an ultraviolet sterilization line lamp according to an embodiment of the present disclosure.
Figure 2:
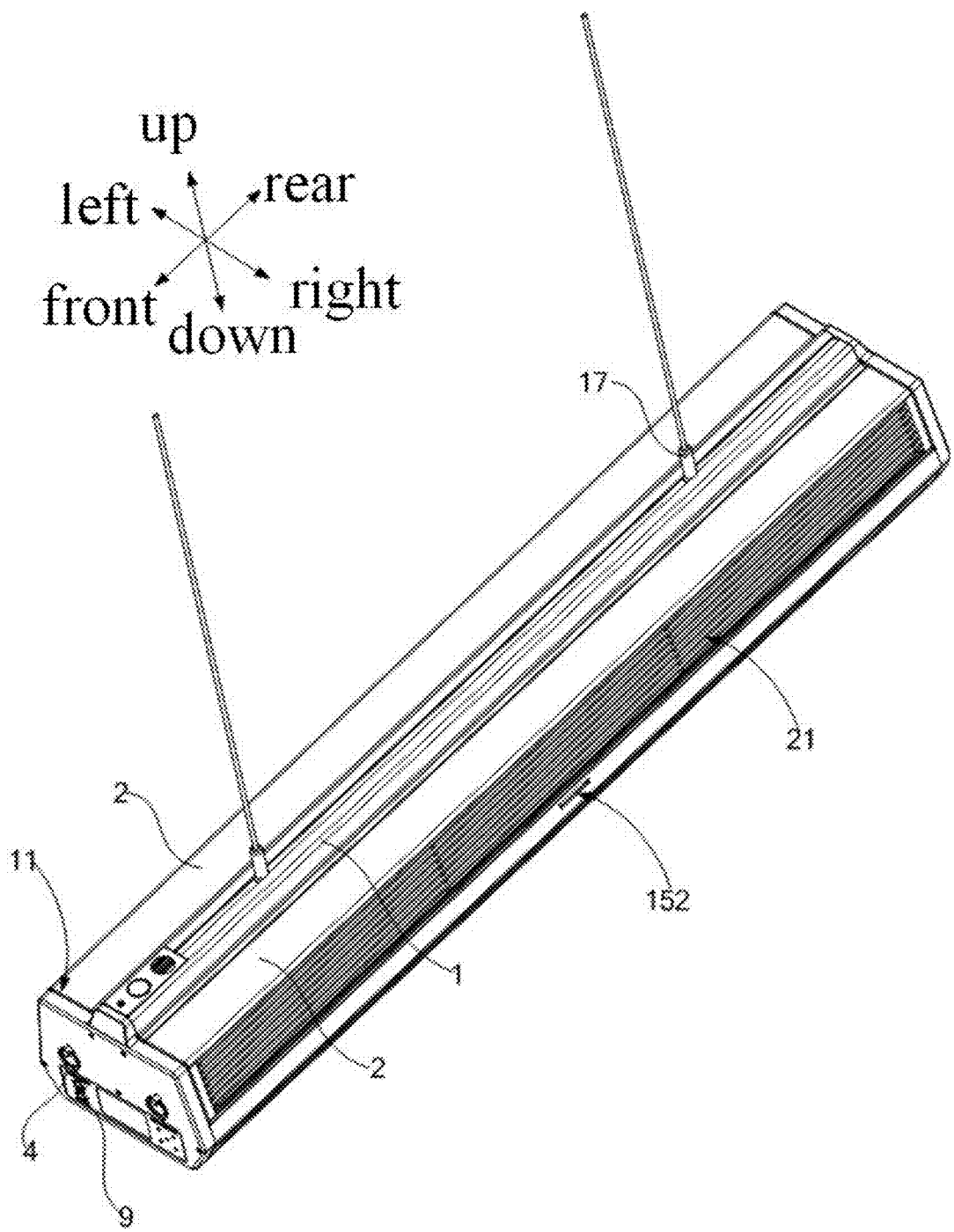
FIG. 2 is a schematic structural diagram of the ultraviolet sterilization line lamp of FIG. 1 from another perspective.
Figure 3:
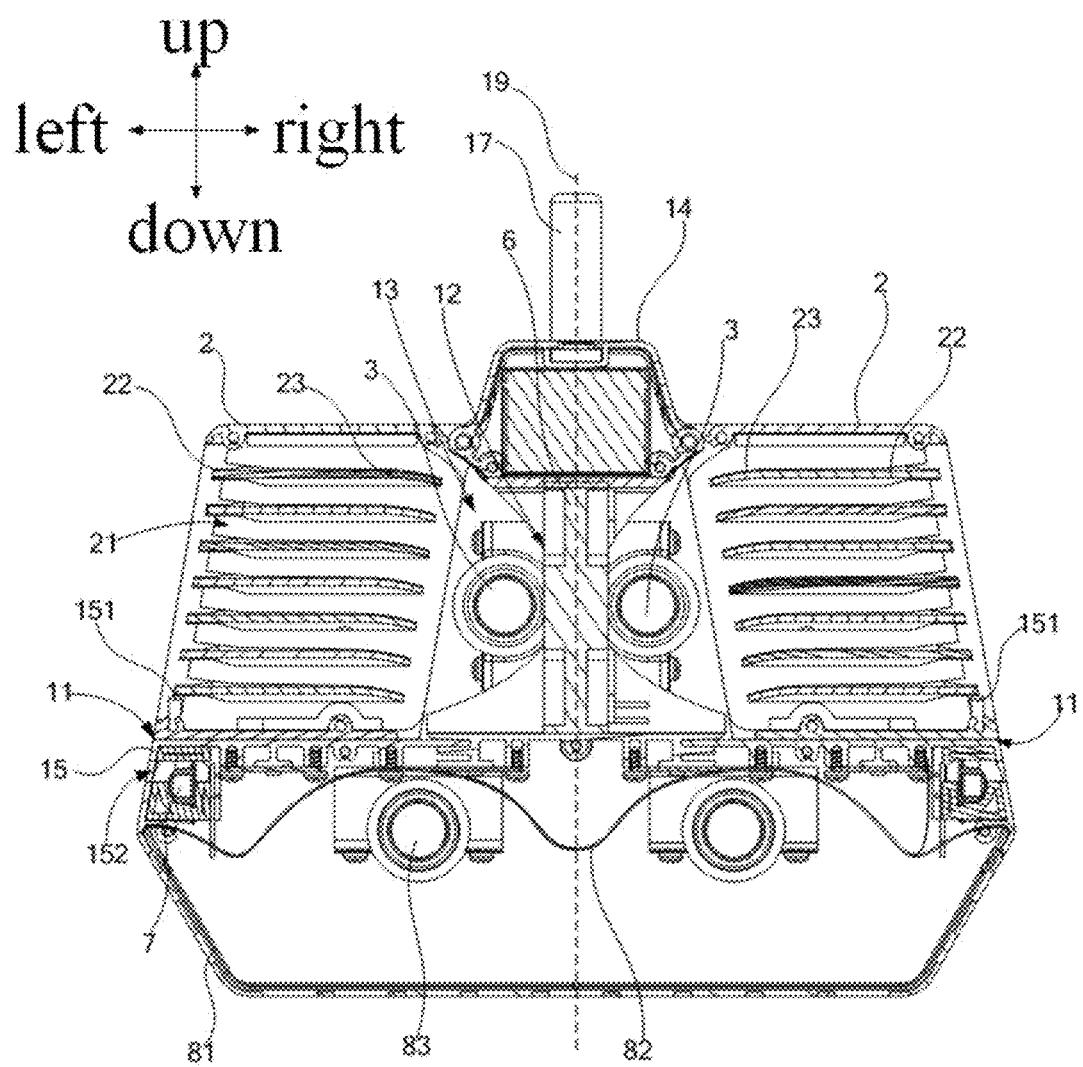
FIG. 3 is a schematic cross-sectional structural diagram of the ultraviolet sterilization line lamp of FIG. 1.
Figure 4:
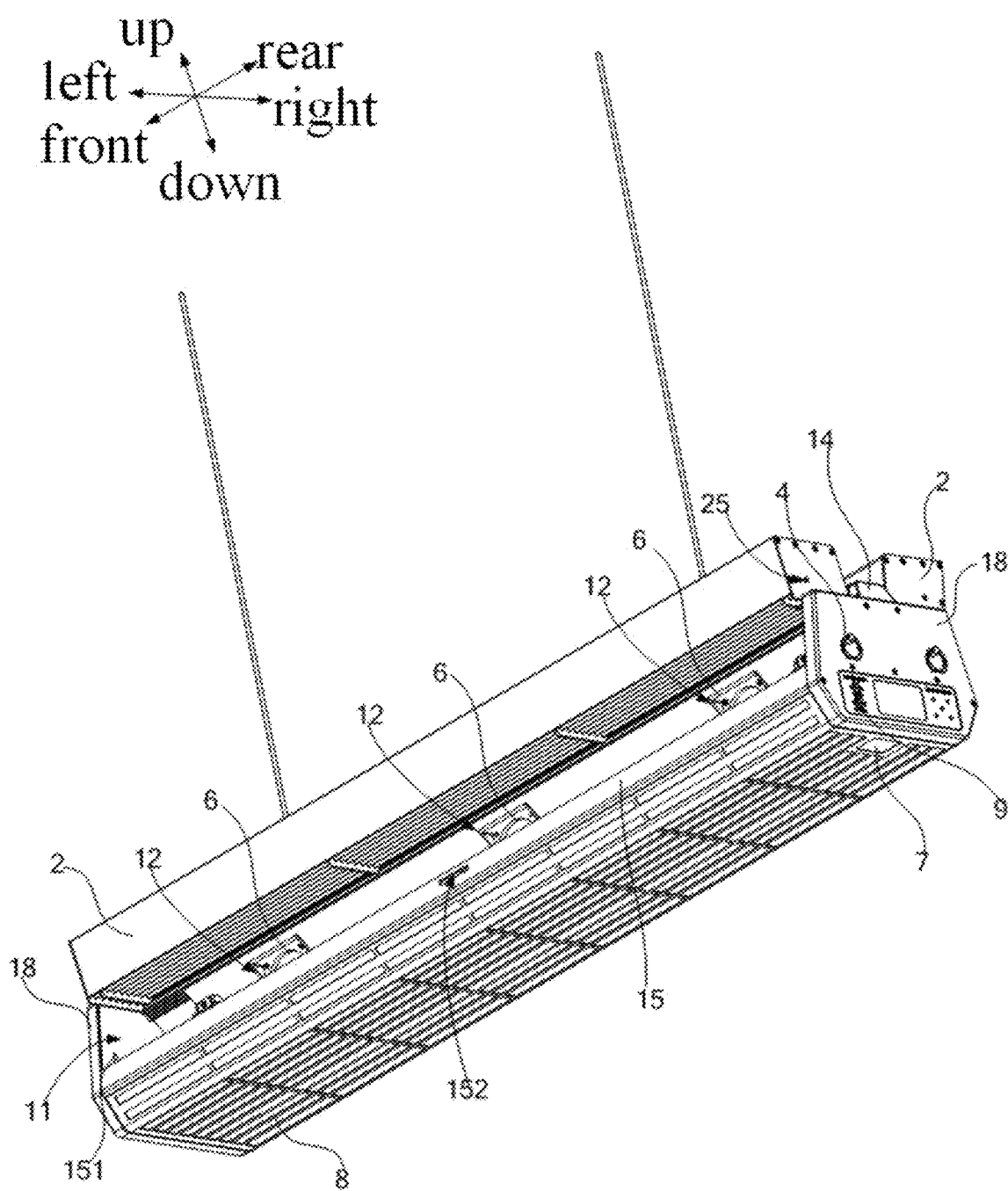
FIG. 4 is a schematic structural diagram of the ultraviolet sterilization line lamp of FIG. 1 in an unfolded state.
Figure 5:
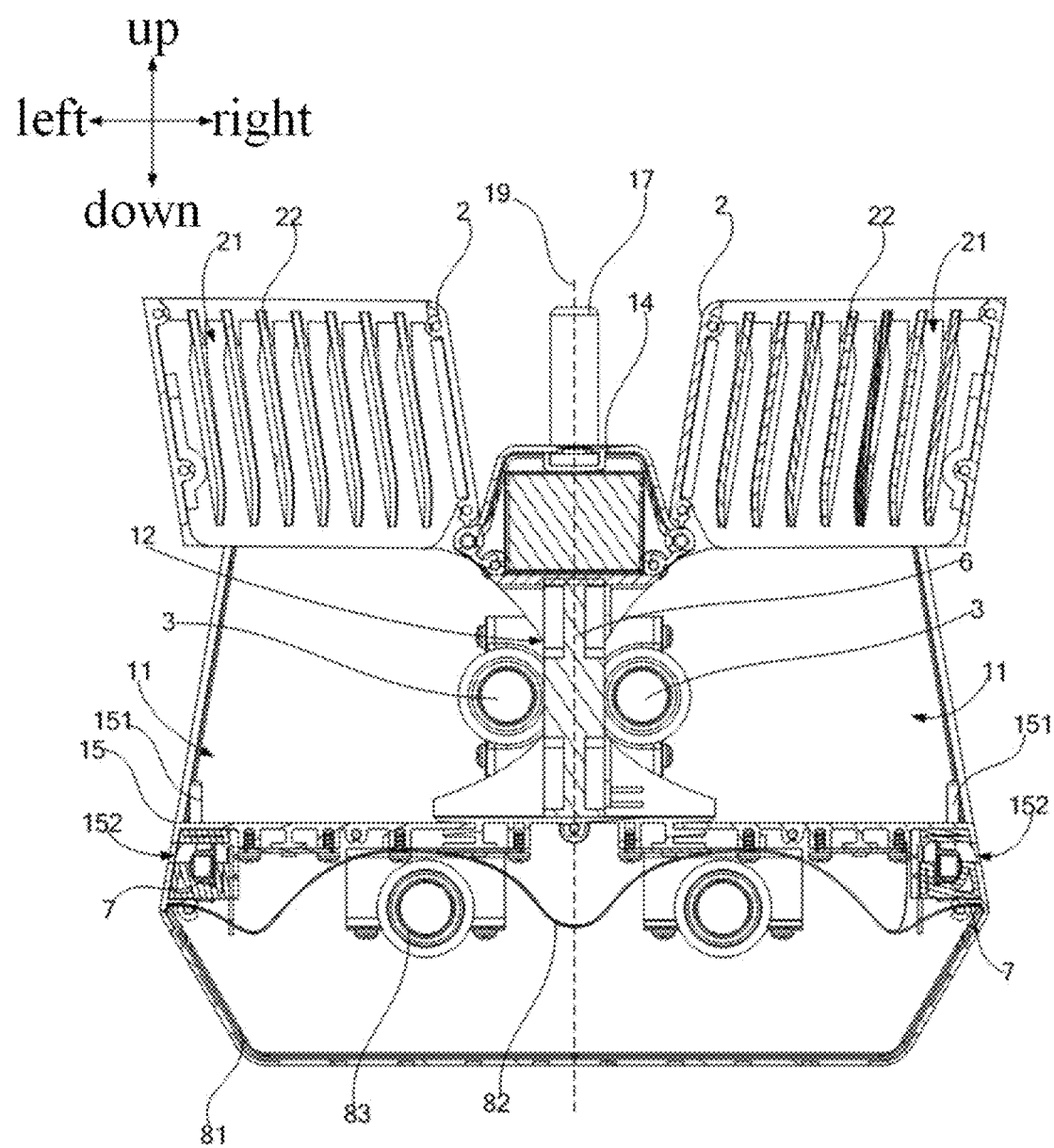
FIG. 5 is a schematic cross-sectional structural diagram of the ultraviolet sterilization line lamp of FIG. 4.
Figure 6:
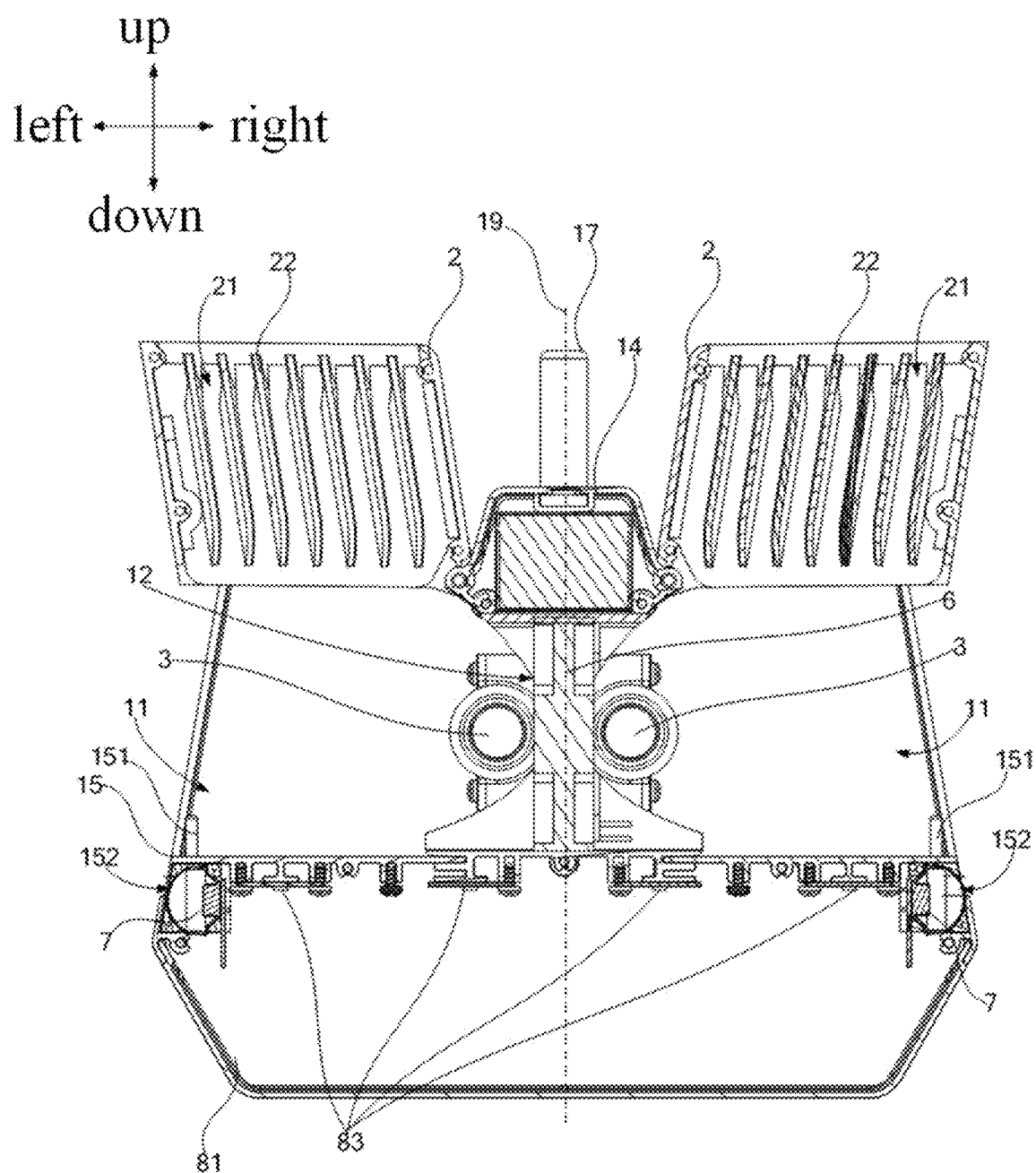
FIG. 6 is a schematic cross-sectional structural diagram of the ultraviolet sterilization line lamp of FIG. 4 according to another embodiment.
Figure 7:
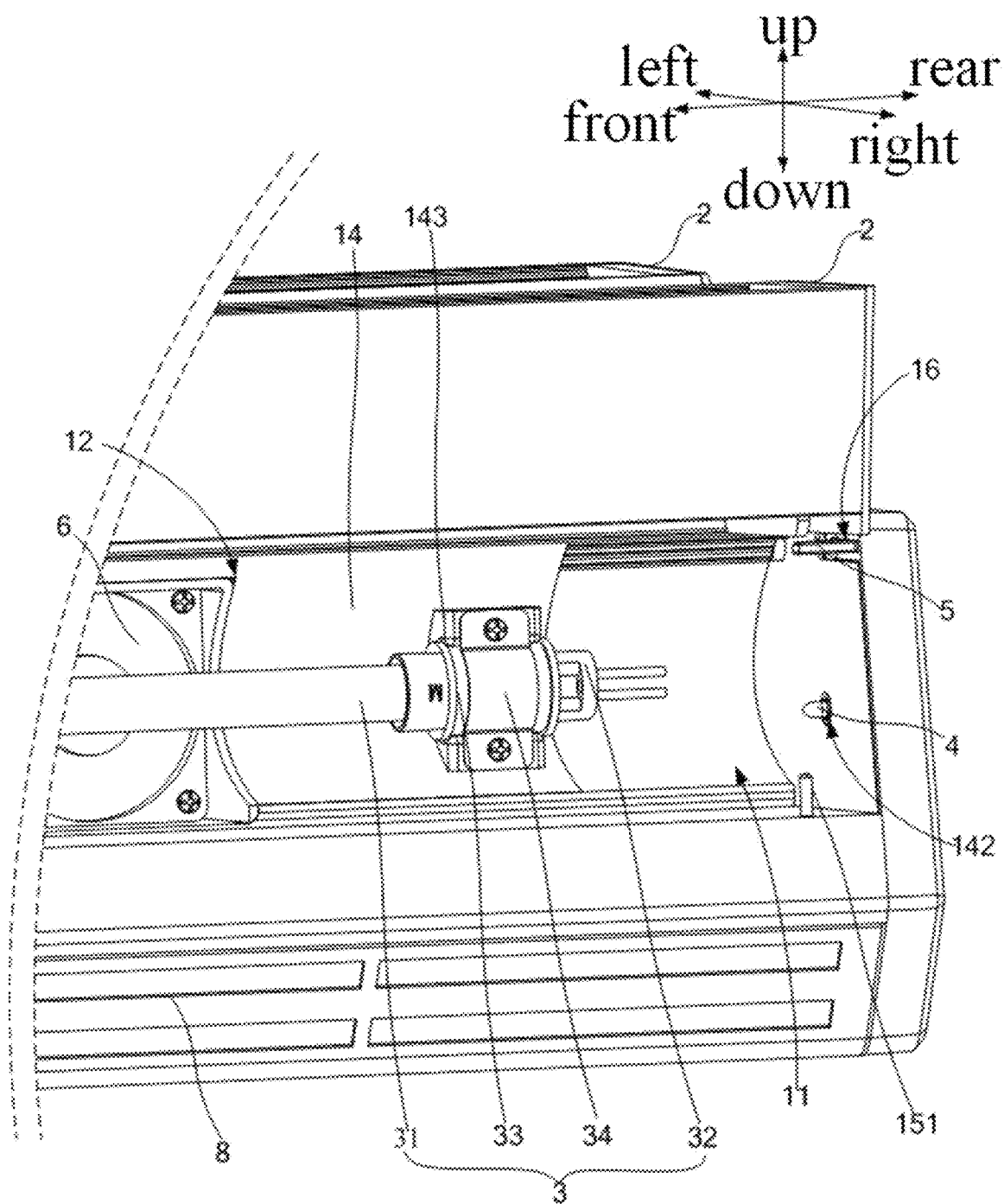
FIG. 7 is a schematic partial structural diagram of the ultraviolet sterilization line lamp of FIG. 4.
Figure 8:
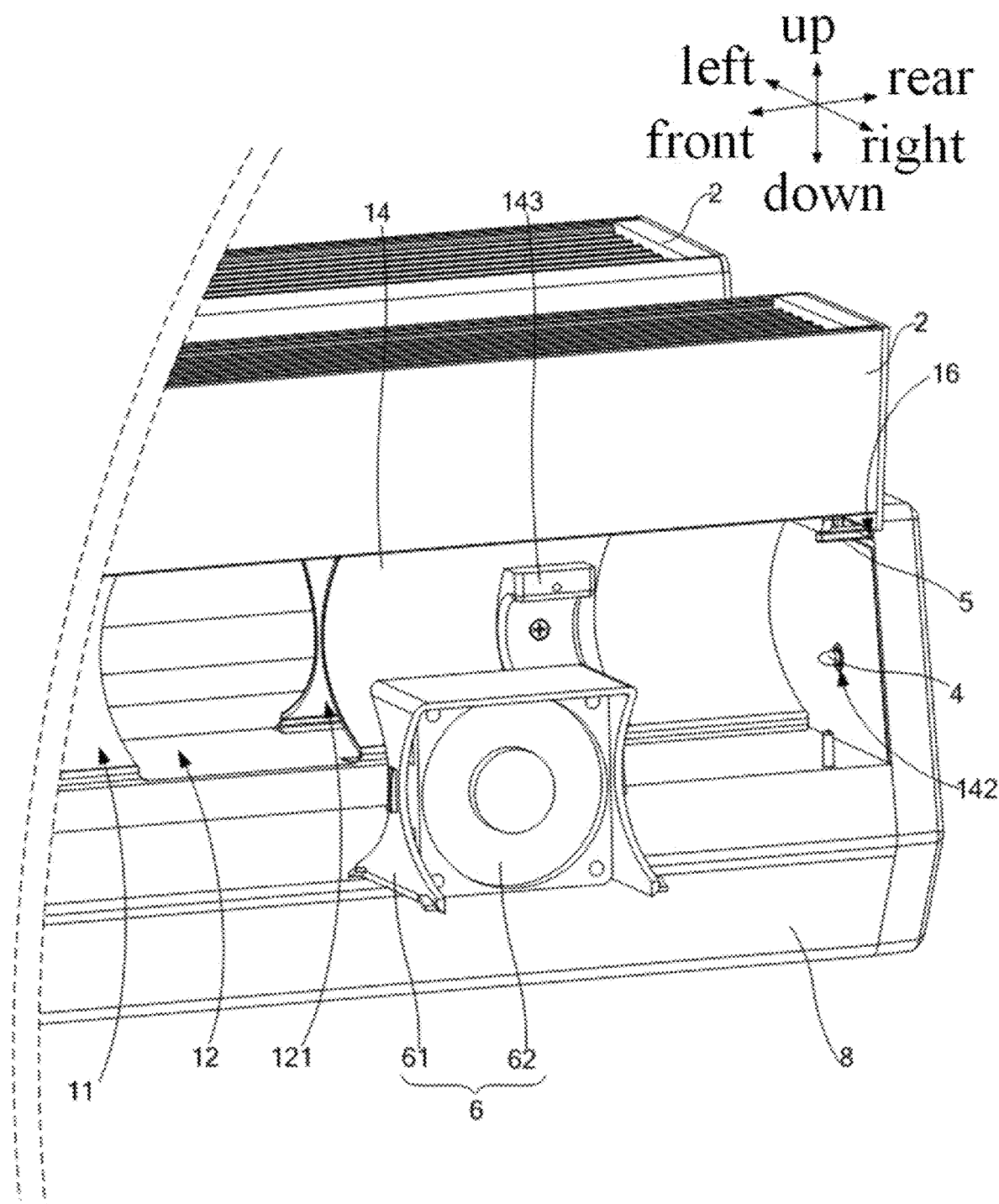
FIG. 8 is a schematic structural diagram of the assembly of a fan module and a lamp body of FIG. 7.
Figure 9:
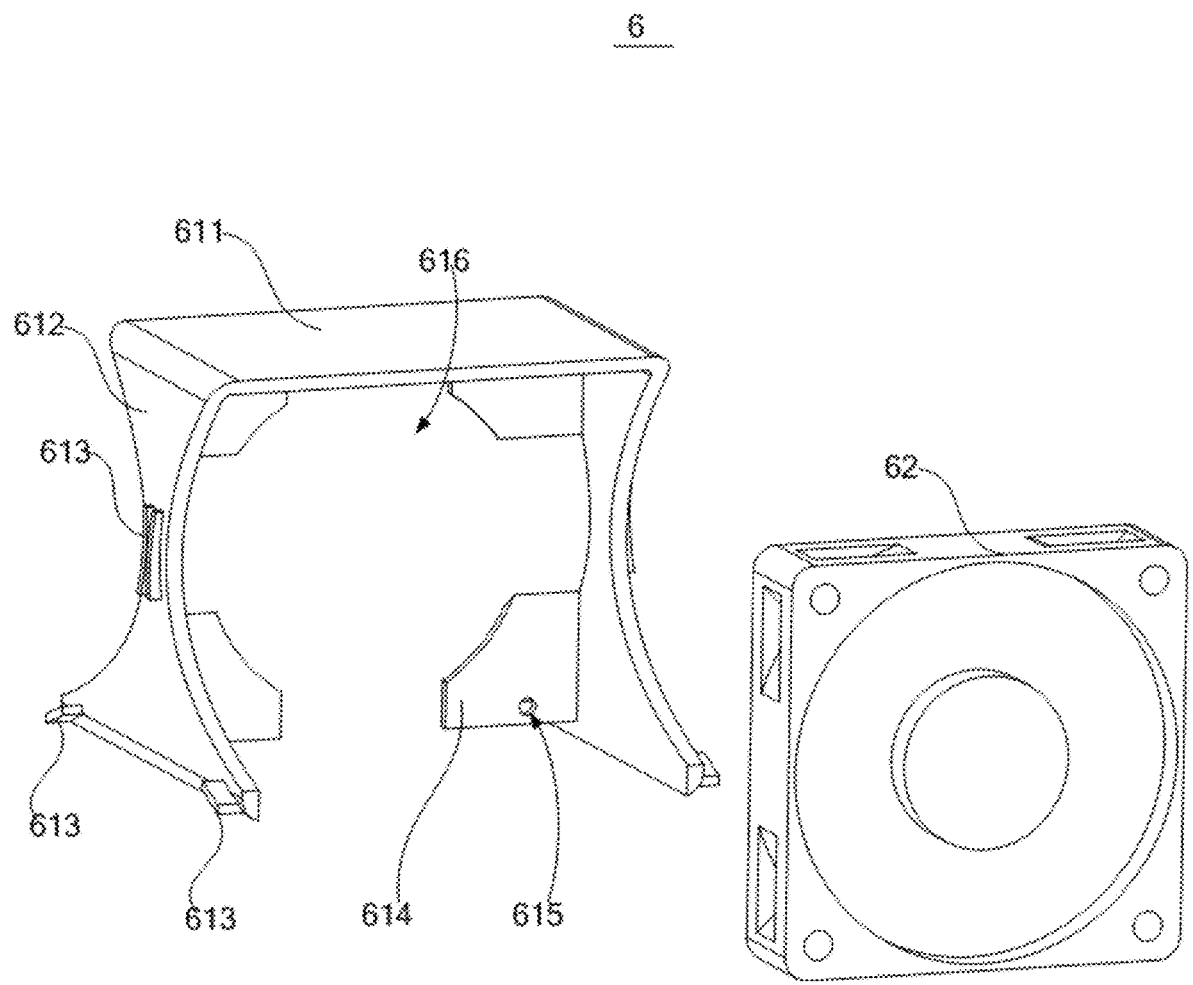
FIG. 9 is a schematic structural diagram of the assembly of a fan and a mounting bracket of FIG. 8. The realization of the objective, functional characteristics, and advantages of the present disclosure are further described with reference to the accompanying drawings.

The present disclosure provides an ultraviolet sterilization line lamp. As shown in FIG. 1, FIG. 1 is a schematic structural diagram of the ultraviolet sterilization line lamp according to an embodiment of the present disclosure; as shown in FIG. 2, FIG. 2 is a schematic structural diagram of the ultraviolet sterilization line lamp of FIG. 1 from another perspective; as shown in FIG. 3, FIG. 3 is a schematic cross-sectional structural diagram of the ultraviolet sterilization line lamp of FIG. 1; as shown in FIG. 4, FIG. 4 is a schematic structural diagram of the ultraviolet sterilization line lamp of FIG. 1 in an unfolded state; as shown in FIG. 5, FIG. 5 is a schematic cross-sectional structural diagram of the ultraviolet sterilization line lamp of FIG. 4; as shown in FIG. 6, FIG. 6 is a schematic cross-sectional structural diagram of the ultraviolet sterilization line lamp of FIG. 4 according to another embodiment; as shown in FIG. 7, FIG. 7 is a schematic partial structural diagram of the ultraviolet sterilization line lamp of FIG. 4; as shown in FIG. 8, FIG. 8 is a schematic structural diagram of the assembly of a fan module and a lamp body of FIG. 7; as shown in FIG. 9, FIG. 9 is a schematic structural diagram of the assembly of a fan and a mounting bracket of FIG. 8.

In an embodiment of the present disclosure, as shown in FIG. 1 to FIG. 6, the ultraviolet sterilization line lamp includes a lamp body 1, two grilles 2 and two ultraviolet sterilization modules 3. The lamp body 1 is elongated, and two sides of the lamp body 1 are provided with two accommodating grooves 11. The two grilles 2 are connected to the lamp body 1 and respectively located in the two accommodating grooves 11. Inner wall surfaces of each of the grilles 2 and each of the accommodating grooves 11 form a sterilization cavity 13, each of the grilles 2 includes light exit grooves 21 communicating with the sterilization cavity 13, each of the light exit grooves 21 extends from one end of a corresponding grille 2 close to the lamp body 1 to another end of the corresponding grille 2 away from the lamp body 1, an inner wall surface of each of the light exit grooves 21 is provided with a light-absorbing layer; and the two ultraviolet sterilization modules 3 are connected to the lamp body 1 or the grille 2, and respectively located in two sterilization cavities 13.

It should be understood that a length direction of the lamp body 1 is a front-rear direction of the lamp body 1, a direction of the lamp body 1 to the grilles 2 on both sides is a left-right direction, and a direction of the lamp body 1 away from the ground to close to the ground is an up-down direction. The two grilles 2 are provided at the left direction and right direction of the lamp body 1, respectively.

In this embodiment, the two grilles 2 are provided on opposite sides of the lamp body 1, and the ultraviolet sterilization module 3 is provided between the lamp body 1 and the grille 2, such that the ultraviolet rays generated by the ultraviolet sterilization module 3 are emitted from the grille 2 on both sides of the lamp body 1. The ultraviolet sterilization line lamps are usually hoisted or directly installed on the ceiling. Ultraviolet rays are emitted from the grille 2 on both sides of the lamp body 1 to prevent ultraviolet rays from irradiating the human body and improve the safety of the ultraviolet sterilization line lamp. In addition, one end of the light exit groove 21 of the grille 2 is away from the lamp body 1, so that ultraviolet rays can be directly emitted into the environment outside the lamp, and the sterilization effect of the air in the surrounding environment of the grille 2 is improved. Ultraviolet rays are directly emitted towards the areas corresponding to the two grilles 2 to increase the sterilization range of ultraviolet rays on the air in the environment. Meanwhile, under the action of air convection, the sterilized air can be discharged as soon as possible and the unsterilized air can enter the sterilization area directly exposed to ultraviolet rays as soon as possible, thereby improving the sterilization efficiency of the overall space. Even without a fan, a good sterilization effect can be obtained. On the other hand, the light exit grooves 21 are provided on the grille 2, and the light exit grooves 21 extend from one end of the grille 2 close to the lamp body 1 to the other end of the grille 2 away from the lamp body 1. In other words, the light exit groove 21 of the grille 2 has a longer covering length, and the surface of the light exit groove 21 is provided with a light-absorbing layer that absorbs ultraviolet rays. When the ultraviolet rays are irradiated in the direction of the grille 2, except for the ultraviolet rays parallel to the inner wall surface of the light exit groove 21 can be emitted from the lamp, other ultraviolet rays will be absorbed by the inner wall surface of the light exit groove 21, reducing the probability of ultraviolet rays directly irradiating the human body, and enhancing the safety of the ultraviolet sterilization line lamp. The ultraviolet sterilization line lamp of the present disclosure improves the safety of environmental sterilization by ultraviolet rays and improves the sterilization effect.

In an embodiment, the light exit groove 21 of the grille 2 emits ultraviolet rays horizontally, obliquely upward, or vertically upward, which can achieve the effect of safe use.

In an embodiment, the accommodating groove 11 is configured as a reflective surface. It should be understood that a mirror layer is provided on the inner wall surface of the accommodating groove 11. Or, the inner wall surface of the accommodating groove 11 is coated with a reflective coating. Or, a reflective film is pasted on the inner wall surface of the accommodating groove 11. Or, the inner wall surface of the accommodating groove is polished to form a reflective surface.

In the application of this embodiment, the ultraviolet sterilization module 3 can have two settings. The ultraviolet sterilization module 3 can adopt a scheme of an ultraviolet lamp tube to emit light; or, the ultraviolet sterilization module 3 can adopt a scheme of a LED ultraviolet lamp bead to emit light, as follows:

When the ultraviolet sterilization module 3 can adopt the scheme of ultraviolet lamp tube to emit light, the ultraviolet lamp tube can be installed on the lamp body 1 or the grille 2, and the ultraviolet lamp tube corresponds to the light exit grooves 21. In order to improve the light utilization rate of the ultraviolet lamp tube, a reflective surface structure may be provided on the inner wall surface of the accommodating groove 11, such that the light of the ultraviolet lamp tube can be reflected by the reflective surface structure and then transmitted from the light exit groove 21, which improves the energy utilization rate and enhances the sterilization effect.

When the ultraviolet sterilization module 3 can adopt the scheme of LED ultraviolet lamp bead to emit light, the LED ultraviolet lamp bead can be installed on the lamp body or the grille 2 so that the LED ultraviolet lamp bead corresponds to the light exit groove 21. When the LED ultraviolet lamp bead is installed on the lamp body 1, the LED ultraviolet lamp bead is facing the light exit groove 21; when the LED ultraviolet lamp bead is installed on the grille 2, the LED ultraviolet lamp bead can be partially extended into the light exit groove 21.

In an embodiment of the present disclosure, the lamp body 1 can have various implementation forms. For example, the accommodating grooves 11 on both sides of the lamp body 1 are sink grooves or open grooves. Take the following two cases as examples:

In the first case, the accommodating grooves 11 on both sides of the lamp body 1 may be sink grooves; that is, sink grooves are provided in the left-right direction of the lamp body 1. That is to say, the two grilles 2 can be at least partially embedded in the containing groove 11.

In the second case, the accommodating grooves 11 on both sides of the lamp body 1 may be open grooves; that is, open grooves are provided in the left-right direction of the lamp body 1. That is to say, two sides of the lamp body 1 extend to form bosses on both sides of the lamp body 1, and the bosses on both sides of the lamp body 1 cooperate with the lamp body 1 to form open grooves. It can be considered that the boss is provided below the grille 2.

In the application of the above-mentioned embodiment, the grille 2 and the lamp body 1 can be assembled by snap connection, plug-in fitting, screw locking, and the like. Understandably, the boss can be used to support the grille 2; on the other hand, the boss can also shield the ultraviolet grille 2 to prevent ultraviolet rays from being emitted from the gap between the grille 2 and the lamp body 1.

In an embodiment of the present disclosure, as shown in FIG. 1, the ultraviolet sterilization line lamp further includes a mounting portion 17. Understandably, a mounting position may be provided on the lamp body 1, and the mounting portion 17 is limited to a mounting position. The mounting portion 17 is connected to the lamp body 1. Taking the mounting portion 17 as a connection piece, an end of the mounting portion 17 away from the lamp body 1 can be connected to the ceiling. The hoisting clamp can usually be connected to a rope, and the other end of the rope is connected to the ceiling. Or, the hoisting clamp can also be a long rod, and the rod is directly connected to the ceiling.

In an embodiment, the mounting position can be a chute, a threaded hole or a pin hole, etc. Taking the mounting position as a chute as an example, the chute can be provided along the length of the lamp body 1, and a notch of the chute is provided as a narrowing. The mounting portion 17 is a hoisting clamp, which is clamped in the chute and can move along the chute.

In an embodiment of the present disclosure, as shown in FIG. 3, FIG. 5 and FIG. 6, each of the light exit grooves 21 extends from one end of the grille 2 close to the lamp body 1 to the other end of the grille 2 away from the lamp body 1. It can be considered that each of the light exit grooves is centered on the lamp body 1 and extends in the left-right direction of the lamp body 1.

In the application of the above-mentioned embodiments, as shown in FIG. 1, taking a central symmetry plane of the lamp body 1 as a reference plane 19, the two accommodating grooves 11 are mirror images of the reference plane 19. In other words, the central symmetry plane of the lamp body 1 is a vertical plane perpendicular to the ground, and the vertical plane is provided along the length direction of the lamp body 1. Taking the direction perpendicular to the reference plane 19 as the horizontal direction, the light exit groove 21 may be parallel to the horizontal direction; or, the light exit groove 21 may form an angle with the horizontal direction.

In an embodiment of the present disclosure, the light exit groove 21 may form an angle with the horizontal direction. The extending direction of the light exit groove 21 away from the notch of the lamp body 1 is an oblique upward direction. When the ultraviolet rays are emitted from the light exit groove 21, the ultraviolet rays can be emitted upwards to prevent the ultraviolet rays from being emitted to the user.

In an embodiment of the present disclosure, as shown in FIG. 3, FIG. 5 and FIG. 6, each of the grilles 2 includes light-absorbing plates 22 provided in the left-right direction; or, provided in the up-down direction.

On one hand, as shown in FIG. 3, FIG. 5 and FIG. 6, the light-absorbing plates 22 are provided in the left-right direction, which means that each of the light-absorbing plates 22 is provided along a length direction of the lamp body 1, and an extension surface of each of the light-absorbing plates 22 is perpendicular to the reference plane 19, and two adjacent light-absorbing plates 22 are spaced apart and form a light exit groove 21. The length direction is the front-rear direction of the lamp body 1.

On the other hand, the light-absorbing plates 22 are provided in the up-down direction, which means that each of the light-absorbing plates 22 is provided along a thickness direction of the lamp body 1, and an extension surface of each of the light-absorbing plates 22 is perpendicular to the reference plane 19, and two adjacent light-absorbing plates 22 are spaced apart and form a light exit groove 21. The thickness direction is the up-down direction of the lamp body 1.

In an embodiment of the present disclosure, taking a central symmetry plane of the lamp body 1 as a reference plane 19, the two accommodating grooves 11 are mirror images of the reference plane 19.

Each of the grilles 2 includes light-absorbing plates 22 along a length of the lamp body 1, an extension surface of each of the light-absorbing plates 22 is perpendicular to the reference plane 19, two adjacent light-absorbing plates 22 are spaced apart and configured to form the light exit groove 21; a surface of each of the light-absorbing plates 22 is provided with the light-absorbing layer; and each of the two accommodating grooves 11 is configured as a reflective surface.

In this embodiment, the extension surface of each of the light-absorbing plates 22 is perpendicular to the reference surface 19 to form the light exit grooves 21 perpendicular to the reference surface 19. When the ultraviolet sterilization module 3 emits ultraviolet rays, the ultraviolet rays can be emitted out of the grille 2 in parallel to sterilize the air in the parallel direction of the grille 2. As for the space below the grille 2, ultraviolet rays cannot be directly irradiated to the bottom, and the ultraviolet rays are prevented from directly irradiating the space below, which can ensure the safety of users in the space below. On the other hand, the accommodating groove is configured as the reflective surface, such that the intensity of the ultraviolet rays emitted from the grille can be higher, and the utilization rate of the ultraviolet rays can be improved.

In an embodiment of the present disclosure, the light-absorbing layer may be a coating coated on the surface of the light-absorbing plate 22; or, the light-absorbing layer may be a structure in which metal is deposited on the surface of the light-absorbing plate 22; or, the light-absorbing layer may be a diffuse reflection layer formed by physical polishing.

In an embodiment of the present disclosure, as shown in FIG. 3, each of the light-absorbing plates 22 is provided with a bending portion 23 at one end adjacent to a corresponding ultraviolet sterilization module 3. That is to say, one end of the light-absorbing plate 22 adjacent to the ultraviolet sterilization module 3 is bent to form the bending portion 23, so that one end of the light exit groove 21 formed by two adjacent light-absorbing plates 22 is a bending groove body. After the ultraviolet sterilization module 3 emits ultraviolet rays, the ultraviolet rays are partially blocked by the bending portion 23 of the light-absorbing plate 22, which reduces the intensity of the ultraviolet rays emitted to the outside, thereby improving the safety of the ultraviolet sterilization line lamp.

In an embodiment of the present disclosure, as shown in FIG. 4, FIG. 7 and FIG. 8, the lamp body 1 is further provided with a through hole 12 communication with the two accommodating grooves 11; and the ultraviolet sterilization line lamp further includes a fan module 6 provided on the lamp body 1 and located at the through hole 12, to enhance the air flow through the lamp body 1, thereby enhancing the sterilization effect.

In the application of this embodiment, when the fan module 6 is installed at the through hole 12, the air inlet surface of the fan module 6 is towards the light exit groove 21 of any grille 2. When the left and right grilles 2 and the fan module 6 are horizontally provided, the air inlet and outlet of the fan module 6 will be smoother, which can reduce the power consumption of the fan module 6 and reduce noise.

In an embodiment of the present disclosure, as shown in FIG. 4, the lamp body 1 is further provided with through holes 12 provided along the length direction of the lamp body 1. The ultraviolet sterilization line lamp further includes fan modules 6 respectively provided at the through holes 12.

In an embodiment of the present disclosure, as shown in FIG. 3, FIG. 5 and FIG. 6, the lamp body 1 includes a first frame 14 and a second frame 15. The second frame 15 is provided on a side of the first frame 14 and forms an angle with the first frame 14. The first frame 14 and the second frame 15 form two accommodating grooves 11. The two grilles 2 are connected to the first frame 14 and/or the second frame 15 respectively, and are enclosed with the second frame 15 to form a sterilization cavity 13. The ultraviolet sterilization module 3 is connected to the second frame 15 and is located in the sterilization cavity 13.

In an embodiment, a mounting position is provided on the first frame 14, and the hoisting clamp and the first frame 14 is away from an end surface of the second frame 15.

In an embodiment of the present disclosure, as shown in FIG. 3, each of the grilles 2 includes light-absorbing plates 22, and the light-absorbing plates 22 are all parallel to the second frame 15, and two adjacent light-absorbing plates 22 are spaced apart to form a light exit groove 21.

In an embodiment of the present disclosure, a surface of each of the light-absorbing plates 22 is a corrugated surface to increase the surface area of the light-absorbing plate 22 and improve the light absorption efficiency.

In an embodiment of the present disclosure, as shown in FIG. 8 and FIG. 9, a limiting space 121 is provided on a periphery of the through hole 12; that is, the first frame 14 is provided with an inner cavity corresponding to the through hole 12, and the cavity wall of the inner cavity forms the limiting space 121. Understandably, the first frame 14 may be an aluminum alloy extruded part, a middle of the aluminum alloy extruded part is hollow, and the through hole 12 penetrates a side wall of the aluminum alloy extruded part.

As shown in FIG. 9, the fan module 6 includes a mounting bracket 61 and a fan 62 connected to the mounting bracket 61, the mounting bracket 61 is provided with an escape space 616 corresponding to the fan 62, an outer wall surface of the mounting bracket 61 is provided with a clamping portion 613, and the clamping portion 613 is configured to abut against an inner wall surface of the limiting space 121. That is, the mounting bracket 61 abuts or clamps with the inner wall surface of the first frame 14 through the clamping portion 613, avoiding the use of screws between the mounting bracket 61 and the lamp body 1, which can improve the efficiency of disassembly and assembly.

In an embodiment, the clamping portion 613 may be a protrusion, and the protrusion abuts against the inner wall surface of the limiting space 121 to hold the mounting bracket 61 on the lamp body 1.

In an embodiment, the clamping portion 613 includes two protrusions, the two protrusions form a limiting gap, and the peripheral wall surface of the through hole 12 is limited within the limiting gap.

In an embodiment, the clamping portion 613 includes protrusions spaced apart. The protrusions are accommodated in the limiting space 121 and abut against the inner wall surface of the limiting space 121 to position the mounting bracket 61 on the lamp body 1.

In an embodiment, the mounting bracket 61 and the fan 62 can be locked with screws. Or, the mounting bracket 61 and the fan 62 may be a snap-fit connection.

In an embodiment of the present disclosure, as shown in FIG. 9, the mounting bracket 61 includes a first plate 611 and two second plates 612. The first plate 611 has two ends. The two second plates 612 are respectively connected to both ends of the first plate 611. The two second plates 612 protrude from the same side surface of the first plate 611 and are enclosed to form an escape space 616. A surface of the second plate 612 facing away from the escape space 616 is protrudingly provided with a clamping portion 613. A surface of the second plate 612 facing the escape space 616 is provided with a mounting protrusion 614 for mounting the fan 62.

When assembling the mounting bracket 61 and the first frame 14, based on the elastic deformation between the first plate 611 and the second plate 612, the user can hold the mounting bracket 61 and squeeze one end of the two second plates 612 away from the first plate 611 to make the two second plates 612 move closer or farther away. The mounting bracket 61 is pushed into the through hole 12 of the first frame 14 as a whole. When the user removes the force acting on the second plate 612, the second plate 612 returns to the original state relative to the first plate 611, such that the clamping portion 21 is snap-fitted with the escape space 616 of the inner wall surface of the through hole 12, and the mounting bracket 61 is connected to the first frame 14. The mounting bracket 61 of the present disclosure is simple to assemble, easy to disassemble and assemble, high in installation efficiency, and compact in structure, which can avoid noise.

In an embodiment of the present disclosure, as shown in FIG. 9, the mounting protrusion 614 is provided with a mounting hole 615, and the mounting hole 615 corresponds to the hole on the fan 62. The screw passes through the mounting hole 615 and the hole on the fan 62 to mount the fan 62 on the mounting protrusion 614.

In an embodiment of the present disclosure, as shown in FIG. 3, FIG. 5 and FIG. 6, the lamp body 1 is provided with two first shaft holes (not shown) corresponding to the two accommodating grooves 11; and each of the grilles 2 is provided with a second shaft hole (not shown), a rotating shaft passes through one of the two first shaft holes and the second shaft hole corresponding to one of the first shaft holes to rotationally connect the two grilles 2 with the lamp body 1.

In this embodiment, the user can rotate the grille 2 to expose the ultraviolet sterilization module 3 to facilitate the maintenance of the ultraviolet sterilization module 3.

Based on the above embodiment, two first shaft holes are provided at one end of the first frame 14 away from the second frame 15, and the two first shaft holes are respectively adjacent to the two accommodating grooves 11. Each of the grilles 2 is provided with a second shaft hole, and the rotating shaft passes through a first shaft hole and a second shaft hole corresponding to the first shaft hole, so that the two grilles 2 are rotatably connected with the first frame 14.

In an embodiment of the present disclosure, as shown in FIG. 4 and FIG. 7, the lamp body 1 is provided with a first insertion hole 142 communicating with the accommodating groove 11. The grille 2 is provided with a second insertion hole 25 corresponding to the first insertion hole 142. The ultraviolet sterilization line lamp further includes a fixing pin 4 penetrating through the first insertion hole 142 and the second insertion hole 25 to lock the grille 2 and the lamp body 1.

In an embodiment of the present disclosure, the lamp body 1 is provided with a first insertion hole 142 communicating with the accommodating groove 11. The ultraviolet sterilization line lamp further includes a fixing pin 4 movably penetrating through the first insertion hole 142. When the grille 2 is configured to rotate relative to the lamp body 1 and open the accommodating groove 11, the fixing pin 4 extends from the first insertion hole 142 into the accommodating groove 11, and abuts against a bottom of the grille 2 to keep the accommodating groove 11 open.

An end of the fixing pin 4 exposed on the outer surface of the lamp body 1 can be provided with a pull ring to improve the convenience of operation.

In an embodiment of the present disclosure, an elastic element is sleeved on the fixing pin 4, the elastic element is connected to a wall surface of the first insertion hole 142; and in an initial state, the elastic element is configured to exert an elastic force on the fixing pin 4, to make the fixing pin 4 partially extend into the accommodating groove 11. Therefore, the fixing pin 4 can automatically rebound after being pulled out, and the fixing pin 4 partially extends into the accommodating groove 11.

In this embodiment, the ultraviolet sterilization line lamp has an unfolded state in which the grille 2 rotates relative to the lamp body 1 so that the accommodating groove 11 is opened, and the ultraviolet sterilization line lamp has a closed state in which the grille 2 closes the accommodating groove 11. In the unfolded state, the fixing pin 4 can extend into the first insertion hole 142, and the fixing pin 4 abuts against the bottom surface of the grille 2 on the side facing the accommodating groove 11. In this way, the accommodating groove 11 is in an open state, so that the user can maintain the ultraviolet sterilization module 3. In the closed state, the fixing pin 4 penetrates through the first insertion hole 142 and the second insertion hole 25 to lock the grille 2 and the lamp body 1.

In an embodiment of the present disclosure, as shown in FIG. 4, the lamp body 1 further includes two end covers 18, which are respectively connected to two ends of the first frame 14 and the second frame 15. Each of the end covers 18 is provided with a first insertion hole 142 communicating with the accommodating groove 11, and the grille 2 is provided with a second insertion hole 25 corresponding to the first insertion hole 142.

In an embodiment of the present disclosure, as shown in FIG. 7, the lamp body 1 is provided with a sliding hole 16 communicating with the accommodating groove 11. The sliding hole 16 is spaced apart from the first insertion hole 142. The ultraviolet sterilization line lamp also includes a limiting block 5 slidably provided on the sliding hole 16. The ultraviolet sterilization line lamp has an unfolded state in which the grille 2 rotates relative to the first frame 14 and is away from the accommodating groove 11. In the unfolded state, the limiting block 5 extends relative to the sliding hole 16 and abuts against the grille 2.

In this embodiment, the limiting block 5 extends relative to the sliding hole 16 and abuts against the grille 2, such that the grille 2 can be in an unfolded state relative to the accommodating groove 11, thereby preventing the grille 2 from being covered with the accommodating groove 11, and improving the safety of the maintenance of the ultraviolet sterilization module 3 by the user.

Based on the above embodiment, as shown in FIG. 7, the end cover 18 is provided with a sliding hole 16 communicating with the accommodating groove 11, and the sliding hole 16 is located at the edge of the end cover 18 away from the second frame 15.

In an embodiment of the present disclosure, as shown in FIG. 7, the lamp body 1 is further provided with an elastic column 151, and the elastic column 151 is provided on a surface of the accommodating groove 11 facing the grille 2. Understandably, the elastic column 151 abuts against the surface of the grille 2. When the fixing pin 4 is withdrawn from the second insertion hole 25, the elastic column 151 bounces the grille 2 for a distance, so as to provide a gap for human hands to reach.

In this embodiment, an elastic column 151 is provided on a surface of the second frame 15 facing the grille 2.

In an embodiment of the present disclosure, the ultraviolet sterilization module 3 includes a lamp tube or a lamp bar.

In an embodiment of the present disclosure, as shown in FIG. 7, the ultraviolet sterilization module 3 includes an ultraviolet sterilization lamp 31, a connection terminal 32, two buffer rings 33 and two pressing rings 34. The two buffer rings 33 are sleeved on an outer surface of a lamp cap of the ultraviolet sterilization lamp 31, the two pressing rings 34 are connected to an inner wall surface of the sterilization cavity 13, thereby the pressing ring 34 is cooperated with the buffer ring 33 to position the ultraviolet sterilization lamp 31 in the sterilization cavity 13, and the connection terminal 32 is electrically connected to the ultraviolet sterilization lamp 31.

In this embodiment, the ultraviolet sterilization lamp 31 is a lamp tube. The lamp caps of the lamp tube are located at both ends of the lamp tube. The buffer ring 33 is provided between the lamp tube and the pressure ring 34 and the lamp body 1 to avoid excessive pressure of the mechanical fit between the lamp tube and the pressure ring 34 and the lamp body 1 and cause damage to the lamp tube. On the other hand, during transportation, the buffer ring 33 can absorb part of the force, reduce the shaking of the ultraviolet sterilization lamp 31, and prevent the ultraviolet sterilization lamp 31 from being damaged.

Based on the above embodiment, the first frame 14 is provided with fixing bases 143 on opposite sides of the first frame 14, and the fixing bases 143 are arc-shaped so as to match the peripheral shape of the ultraviolet sterilization lamp 31. The fixing base 143 is connected to the pressing ring 34 to form an area for limiting the ultraviolet sterilization lamp 31.

In an embodiment of the present disclosure, as shown in FIG. 7, a surface of the accommodating groove 11 facing the ultraviolet sterilization module 3 is a concave arc surface. That is to say, the surface of the first frame 14 facing the ultraviolet sterilization lamp 31 is a concave arc surface.

In this embodiment, the surface of the accommodating groove 11 facing the ultraviolet sterilization module 3 is a concave arc surface, such that the ultraviolet sterilization lamp 31 emits light, and the ultraviolet sterilization lamp 31 illuminates the first frame 14 to reflect the ultraviolet rays to the grille 2, thereby the grille 2 can partially export the ultraviolet rays to the periphery of the grille 2 to improve the sterilization effect.

Based on the above embodiment, the inner wall surface of the accommodating groove 11 is provided with a reflective layer and forms a reflective cover structure, and the reflective cover is curved.

In an embodiment of the present disclosure, as shown in FIG. 1, the ultraviolet sterilization line lamp also includes a sensor 7. Sensing ports of the sensor 7 are provided on both sides of the lamp body 1, and the sensor 7 is spaced apart from the corresponding grille 2.

In this embodiment, when the sensing ports of the sensor 7 are provided on both sides of the lamp body 1, the sensor 7 can be an infrared sensor 7, the sensor 7 provided on both sides of the lamp body 1 is configured to sense whether there is a human body in the space in the horizontal direction of the lamp body 1. When a human body is present, the control circuit of the lamp body 1 is configured to turn off the ultraviolet sterilization module 3.

Based on the above embodiment, as shown in FIG. 1, the two opposite sides of the second frame 15 are provided with escape holes 152, and the two escape holes 152 are respectively located below the two grilles 2, and the sensor 7 is provided on the second frame 15 and corresponding to the escape holes 152. A mounting groove may be provided on the surface of the second frame 15 facing the first frame 14, or a mounting groove may be provided on the surface of the second frame 15 facing the first frame 14, and the escape hole 152 is connected to the mounting groove. The mounting groove is configured to install the sensor 7 to prevent the sensor 7 from being exposed and improve the overall appearance of the ultraviolet sterilization line lamp.

In an embodiment of the present disclosure, as shown in FIG. 1, the lamp body 1 has an up-and-down direction. The ultraviolet sterilization line lamp further includes a sensor 7. The sensing port of the sensor 7 is provided on the surface below the lamp body 1, and the sensor 7 is located under the grille.

In this embodiment, when the sensing port of the sensor 7 is provided on the surface of the second frame 1 away from the grille 2, the sensor 7 can be a microwave sensor 7. The microwave sensor 7 is configured to sense whether there is a human body in the space below the lamp body 1. When there is a human body, it cooperates with the control circuit of the lamp body 1 to turn off the ultraviolet sterilization module 3.

In an embodiment of the present disclosure, as shown in FIG. 5 and FIG. 6, the lamp body 1 has an up-and-down direction, and the ultraviolet sterilization line lamp further includes a light-emitting module 8 provided on the surface below the lamp body 1 and located below the grille 2.

Understandably, the light-emitting module 8 can be configured to emit ultraviolet rays, or the light-emitting module 8 can be configured to emit illumination beams.

In this embodiment, when the light-emitting module 8 is configured to emit ultraviolet rays, the area under the ultraviolet sterilization line lamp can be sterilized. When the light-emitting module 8 is configured to emit illumination beams, it can illuminate the area under the ultraviolet sterilization line lamp.

In an embodiment of the present disclosure, as shown in FIG. 6, when the light-emitting module 8 can be configured to emit illumination beams, the light-emitting module 8 includes a lampshade 81 and a light generating component 83. The light generating component 83 can be provided on the surface of the second frame 15 away from the first frame 14 and the grille 2, and the light generating component 83 is configured to emit illumination beams. The lampshade 81 is connected to the second frame 15 and covers the light generating component 83.

The light generating component 83 may be an LED light bar. The lampshade 81 can be a transparent or semi-transparent photoresist cover.

In an embodiment of the present disclosure, as shown in FIG. 5, when the light-emitting module 8 can be configured to emit ultraviolet rays, the light-emitting module 8 includes a lampshade 81, a reflector 82 and a light generating component 83. The reflector 82 can be provided on the surface of the second frame 15 away from the first frame 14 and the grille 2. The light generating component 83 is provided on the second frame 15 and on the surface of the reflector 82 away from the second frame 15, and the light generating component 83 is configured to emit ultraviolet rays. The lampshade 81 is connected to the second frame 15 and covers the light generating component 83. The lampshade 81 is provided with a plurality of light passing holes.

The light generating component 83 may be an ultraviolet fluorescent tube. The lampshade 81 may be a cover body with light passing holes.

In an embodiment of the present disclosure, as shown in FIG. 1, FIG. 2 and FIG. 4, the ultraviolet sterilization line lamp further includes a control panel 9 provided at the end of the lamp body 1.

In this embodiment, a mounting space corresponding to the control panel 9 can be provided on the end cover 18. The control panel 9 includes a control circuit provided on the end cover 18, a button and an indicator light, and the button and the indicator light are provided on the control circuit. The control circuit is electrically connected to the ultraviolet sterilization module 3, the light-emitting module 8 and the fan module 6.

The above are only some embodiments of the present disclosure, and do not limit the scope of the present disclosure thereto. Under the inventive concept of the present disclosure, equivalent structural transformations made according to the description and drawings of the present disclosure, or direct/indirect application in other related technical fields are included in the scope of the present disclosure.

What is claimed is:

1. An ultraviolet sterilization line lamp, comprising:
   a lamp body, the lamp body being elongated, two sides of the lamp body being provided with two accommodating grooves;
   two grilles connected to the lamp body and respectively located in the two accommodating grooves, inner wall surfaces of each of the grilles and each of the accommodating grooves forming a sterilization cavity, each of the grilles including light exit grooves communicating with the sterilization cavity, each of the light exit grooves extending from one end of a corresponding grille close to the lamp body to another end of the corresponding grille away from the lamp body, an inner wall surface of each of the light exit grooves being provided with a light-absorbing layer; and
two ultraviolet sterilization modules connected to the lamp body or the grille, and respectively located in two sterilization cavities.

2. The ultraviolet sterilization line lamp of claim 1, wherein:
taking a central symmetry plane of the lamp body as a reference plane, the two accommodating grooves are mirror images of the reference plane;
each of the grilles includes light-absorbing plates along a length of the lamp body, an extension surface of each of the light-absorbing plates is perpendicular to the reference plane, two adjacent light-absorbing plates are spaced apart and configured to form a light exit groove;
a surface of each of the light-absorbing plates is provided with the light-absorbing layer; and
each of the two accommodating grooves is configured as a reflective surface.

3. The ultraviolet sterilization line lamp of claim 2, wherein each of the light-absorbing plates is provided with a bending portion at one end adjacent to a corresponding ultraviolet sterilization module.

4. The ultraviolet sterilization line lamp of claim 1, wherein:
the lamp body is further provided with a through hole communication with the two accommodating grooves; and
the ultraviolet sterilization line lamp further includes a fan module provided on the lamp body and located at the through hole.

5. The ultraviolet sterilization line lamp of claim 4, wherein:
a limiting space is provided on a periphery of the through hole;
the fan module includes a mounting bracket and a fan connected to the mounting bracket, the mounting bracket is provided with an escape space corresponding to the fan, an outer wall surface of the mounting bracket is provided with a clamping portion, and the clamping portion is configured to abut against an inner wall surface of the limiting space.

6. The ultraviolet sterilization line lamp of claim 1, wherein:
the lamp body is provided with two first shaft holes corresponding to the two accommodating grooves; and
each of the grilles is provided with a second shaft hole, a rotating shaft passes through one of the two first shaft holes and the second shaft hole corresponding to one of the first shaft holes to rotationally connect the two grilles with the lamp body.

7. The ultraviolet sterilization line lamp of claim 6, wherein:
the lamp body is provided with a first insertion hole communicating with the accommodating groove, and the grille is provided with a second insertion hole corresponding to the first insertion hole; and
the ultraviolet sterilization line lamp further includes a fixing pin penetrating through the first insertion hole and the second insertion hole to lock the grille and the lamp body.

8. The ultraviolet sterilization line lamp of claim 6, wherein:
the lamp body is provided with a first insertion hole communicating with the accommodating groove;
the ultraviolet sterilization line lamp further includes a fixing pin movably penetrating through the first insertion hole; and
when the grille is rotated relative to the lamp body and opens the accommodating groove, the fixing pin is configured to extend from the first insertion hole into the accommodating groove, and abut against a bottom of the grille to keep the accommodating groove open.

9. The ultraviolet sterilization line lamp of claim 8, wherein:
a pull ring is provided at one end of the fixing pin exposed on an outer surface of the lamp body;
an elastic element is sleeved on the fixing pin, the elastic element is connected to a wall surface of the first insertion hole; and
in an initial state, the elastic element is configured to exert an elastic force on the fixing pin, to make the fixing pin extend into the accommodating groove.

10. The ultraviolet sterilization line lamp of claim 7, wherein:
the lamp body is provided with a sliding hole communicating with the accommodating groove, and the sliding hole is spaced apart from the first insertion hole;
the ultraviolet sterilization line lamp further includes a limiting block slidably disposed on the sliding hole;
the ultraviolet sterilization line lamp has an unfolded state, in the unfolded state, the grille is configured to rotate relative to a first frame and be away from the accommodating groove, and the limiting block is configured to extend relative to the sliding hole and abut against the grille; and/or
the lamp body is further provided with an elastic column provided on a surface of the accommodating groove facing the grille.

11. The ultraviolet sterilization line lamp of claim 1, wherein:
the ultraviolet sterilization module includes an ultraviolet sterilization lamp, a connection terminal, two buffer rings and two pressing rings;
the two buffer rings are sleeved on an outer surface of a lamp cap of the ultraviolet sterilization lamp, the two pressing rings are connected to an inner wall surface of the sterilization cavity, thereby the pressing ring is cooperated with the buffer ring to position the ultraviolet sterilization lamp in the sterilization cavity, and the connection terminal is electrically connected to the ultraviolet sterilization lamp; and/or
a surface of the accommodating groove facing the ultraviolet sterilization module is a concave arc surface.

12. The ultraviolet sterilization line lamp of claim 1, wherein the ultraviolet sterilization line lamp further includes a sensor, sensing ports of the sensor are provided on two sides of the lamp body, and the sensor and the grille are spaced apart.

13. The ultraviolet sterilization line lamp of claim 1, wherein the lamp body has an up-down direction, the ultraviolet sterilization line lamp further includes a sensor, a sensing port of the sensor is provided on a surface below the lamp body, and the sensor is located below the grille.

14. The ultraviolet sterilization line lamp of claim 1, wherein the lamp body has an up-down direction, and the ultraviolet sterilization line lamp further includes a light-emitting module provided on a surface below the lamp body and located below the grille.

15. The ultraviolet sterilization line lamp of claim 1, wherein the ultraviolet sterilization line lamp further includes a control panel provided at an end of the lamp body.

\* \* \* \* \*